United States Patent [19]

Horn et al.

[11] 4,182,695
[45] Jan. 8, 1980

[54] POLYAMIDE-FIXED BIOLOGICALLY ACTIVE PROTEIN

[75] Inventors: Jürgen Horn, Langen; Winfried Albert, Pähl; Hans-Georg Batz; Michael Nelböck-Hochstetter, both of Tutzing, all of Fed. Rep. of Germany

[73] Assignee: Boehringer Mannheim GmbH, Waldhof, Fed. Rep. of Germany

[21] Appl. No.: 878,545

[22] Filed: Feb. 16, 1978

[30] Foreign Application Priority Data

Feb. 24, 1977 [DE] Fed. Rep. of Germany ....... 2708018

[51] Int. Cl.² ............... A61K 31/765; A61K 31/775; C08G 69/50
[52] U.S. Cl. ............................... 260/6; 260/7; 260/7.5; 260/8; 260/112 R; 260/112 B; 424/82; 424/85; 424/88; 435/180
[58] Field of Search ............... 260/6, 7, 7.5, 112 R, 260/112 B, 8; 196/63

[56] References Cited

U.S. PATENT DOCUMENTS

| | | | |
|---|---|---|---|
| 3,639,558 | 2/1972 | Csizmas et al. | 195/63 X |
| 3,767,531 | 10/1973 | Olson et al. | 195/63 |
| 3,969,287 | 7/1976 | Jaworek et al. | 260/112 R X |
| 3,970,597 | 7/1976 | Sokolovsky et al. | 260/6 X |
| 4,002,532 | 1/1977 | Weltman et al. | 260/112 R X |
| 4,004,979 | 1/1977 | Avrameas et al. | 260/112 R X |
| 4,046,722 | 9/1977 | Rowland | 260/112 R X |
| 4,066,504 | 1/1978 | Krasnobajew et al. | 260/6 |
| 4,075,194 | 2/1978 | Sela et al. | 424/12 X |
| 4,119,589 | 10/1978 | Horn et al. | 260/6 |

FOREIGN PATENT DOCUMENTS 2603319 8/1977 Fed. Rep. of Germany .

OTHER PUBLICATIONS

Methods in Enzymology, vol. 25, pp. 646–648, Collowick-Kaplan.

Primary Examiner—Howard E. Schain
Attorney, Agent, or Firm—Sprung, Felfe, Horn, Lynch & Kramer

[57] ABSTRACT

Biologically active protein compositions comprising protein or a protein substrate bound onto a polyamide of the general formula:

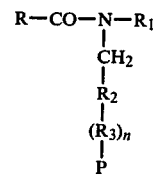

in which
R and $R_1$, which may be the same or different, are polyamide residues bound onto the amido group,
$R_2$ is the residue of a compound which can be condensed with formaldehyde and which contains at least one further reactive group,
$R_3$ is the residue of a bi- or poly-functional protein reagent,
n is 0 or 1, and
P is a biologically active protein;

these compositions are obtainable by the reaction of a polyamides with amounts, equimolar to one another, of formaldehyde and of a compound condensable with formaldehyde, in a solvent for polyamides, reacting the product thereby obtained with a bi- or poly-functional protein reagent and coupling the resulting reaction product with the biologically active protein or protein substrate.

26 Claims, 1 Drawing Figure

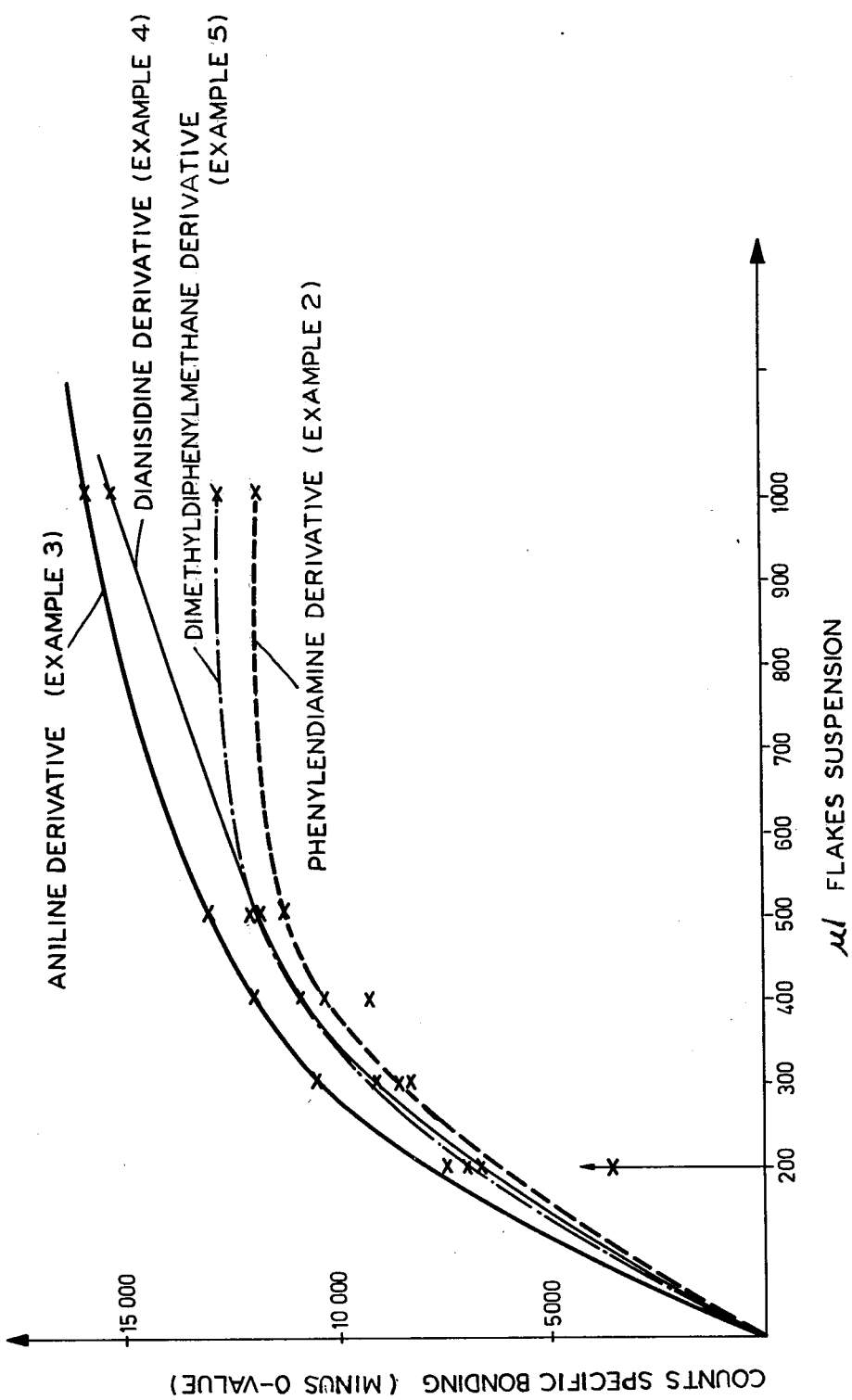

POLYAMIDE-FIXED BIOLOGICALLY ACTIVE PROTEIN

The present invention is concerned with an immobilized, biologically active protein. More specifically, the invention relates to protein substrates fixed on neutral and uncharged polyamide carriers, as well as with a process for the preparation thereof.

The fixing or immobilizing of biologically active proteins, such as enzymes, hormones, substances capable of participation in antigen-antibody reactions and hapten antibody reactions, coagulation factors and the like, has, in recent years, achieved great importance, especially in preparative and analytical chemistry. Although numerous fixing processes have already been developed, new fixing problems continuously arise which cannot be saisfactorily solved with the previously known methods. This is also the reason why, in spite of the clearly obvious advantages of fixing biologically active proteins on to carrier materials, in many fields the introduction of fixed proteins has only taken place slowly in practice and the expected broad breakthrough has not yet been realized.

Because of their interesting physical and chemical properties, polyamides are of especial interest as carrier materials for immobilized active proteins. Due to their content of secondary amino groups, polyamides display a certain chemical similarity with the structure of proteins and especially with regard to their charge distribution, so that adverse effects on the biological activity of enzymes immobilized thereon are small in comparison with other carrier materials, insofar as no other groups are present which disadvantageously influence the activity of the proteins.

Biologically active proteins fixed on polyamide as carrier material are already known in which the protein is bound with the polyamide via amidino structures (cf. for example Collowick-Kaplan "Methods in Enzymology", Vol. 25, pp. 646–648). In analogous manner, polyamides have already also been converted into polyimino esters and coupled with biologically active proteins.

However, in these biologically active proteins immobilized on polyamide, the fundamental favorable properties of the polyamides as carriers for enzymes do not fully manifest themselves because positively charged groups are formed which, in many cases, is disadvantageous for enzyme binding.

Therefore, it is an object of the present invention to provide immobilized enzymes bound on to polyamide in which the binding takes place in such a manner that the carrier remains neutral and uncharged.

According to the present invention, this problem is solved by a biologically active protein or protein substrate covalently bound to polyamide, wherein it is bound via groups of the general formula:

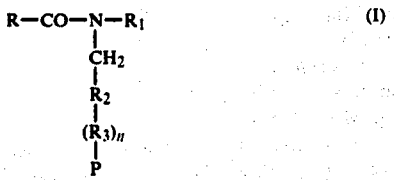
(I)

wherein R and $R_1$, which may be the same or different, are polyamide residues bound on to the amido group, $R_2$ is the residue of a compound which can be condensed with formaldehyde and which contains at least one further reactive group, $R_3$ is the residue of a bi- or polyfunctional protein reagent, n is 0 or 1 and P is a biologically active protein or protein substrate, and is obtainable by the reaction of a polyamide with amounts, equimolar to one another, of formaldehyde and of the compound which can be condensed with formaldehyde in a solvent for polyamides, reaction of the product thereby obtained with a bi- or polyfunctional protein reagent and coupling of the so obtained product with a biologically active protein.

The polyamide used according to the present invention can be not only a uniform polyamide, i.e. a pure or homopolycondensate, to which belong the polycondensates of ω-aminocarboxylic acids and the polycondensates of linear aliphatic diamines and dicarboxylic acids, as well as the polycondensates with aromatic or other components, but also be mixed polyamides. Typical examples include polycaprolactam, polycondensates of adipic acid and hexamethylenediamine (6,6-polyamide), 6,10-polyamide, polyaminoundecanoic acid (11-polyamide), mixed polyamides of caprolactam and dicarboxylic acid diamine salts, such as adipic acid 4,4'-diaminodicyclohexylmethane, 12-polyamide, polycyclamides, such as poly-(1,4-cyclohexylenedimethylenesuperamide), polydodecanol lactam, wool, casein, natural silk, polyarginine and the like.

According to the above definition, R and $R_1$ are the residues of the polyamide bound on to the amido group. These residues can, in turn, contain aliphatic, aromatic or aliphatic-aromatic residues which can contain further secondary or tertiary amino groups, ester groups, amide groups, carboxyl groups, hydroxyl groups or N-substituted carbonamide groups. R and $R_1$ preferably contain straight-chained, branched and/or cyclic alkyl groups or alkylene groups with up to 12 carbon atoms, phenyl groups or phenylene groups or alkylphenylene or alkylenephenylene groups, which, in turn, can be connected together by one or more of the above-mentioned N-substituted carbonamide groups, amide groups, ester groups or the like, peptide chains of natural and/or synthetic amino acids or the like.

The residue $R_2$ is derived from a compound which can be condensed with formaldehyde. This property is fulfilled by substances forming resins with formaldehyde, for example, aromatic compounds containing negative substituents or compounds containing free amino or hydroxyl groups. Apart from the structure or function which can be condensed with formaldehyde, a further functional group must be present which is able to react with a protein reagent. Typical examples of such compounds within the scope of the present invention which can be condensed with formaldehyde and from which the residue $R_2$ is derived include phenol, aniline, urea, thiourea, melamine, diaminotriazine, gelatine, amines, especially aliphatic, aromatic or araliphatic diamines containing 2 to 14 carbon atoms, and alcohols, especially diols and aminoalcohols.

$R_3$ is the residue of a bi- or polyfunctional protein reagent or protein coupling agent, examples of such reagents including dialdehydes, such as gluterdialdehyde, dihydroxysuccinimide esters, diacetals, bis-maleinimides, bifunctional imino esters, such as diethyl malonimidates, dimethyl adipinimidate, diepoxides, dicarboxylic acid chlorides, especially α,β-unsaturated carboxylic acid dichlorides, diisocyanates, diisothiocyanates and the like. They preferably contain 2 to 12 carbon atoms but can also have longer chains. Examples of such longer chained compounds include copolymers of acrylamide/methacrylamide and acrylic acid succinimide esters/methacrylic acid succinimide esters. The abovementioned protein reagents contain two functional groups which can be used for coupling with biologically active proteins in aqueous solution, without impairment of the biological activity thereof. However, according to the present invention, $R_3$ can also be derived from those protein reagents which only contain one protein-binding function or contain more than two such functions. If only one protein-binding group is present, at least one further functional group must be present which is able to react with the further functional group present in the compound which can be condensed with formaldehyde and from which $R_2$ is derived, with the formation of a homopolar bond. Examples of protein reagents which can be used are mentioned in German Patent Specifications Nos. 1,915,970; 2,237,083; 2,128,743; 2,260,185 and 2,603,319. Other protein binding agents from which $R_3$ can be derived include, for example, phosgene, thiophosgene, cyanogen halides and nitrites.

If $R_2$ is derived from an aromatic amine, then the protein binding can be carried out by reaction with a nitrite, i.e. by diazotisation of the aromatic amino group. In this case, a compound is obtained of general formula (I) in which n is 0.

Biologically active proteins which can be used according to the present invention include enzymes, immunologically active proteins, such as antibodies and hormones, as well as biologically active peptides and the like. Instead of biologically active proteins, their substrates can also be fixed.

The present invention also provides a process for fixing biologically active proteins or the substrates thereof on polyamides, wherein a polyamide is reacted in the presence of a solvent for polyamides with amounts, which are equimolar to one another, of formaldehyde and of a compound which can be condensed with formaldehyde and contains at least one further reactive group, with the formation of a polyamide derivative of the general formula:

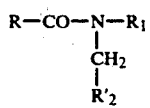

(II)

wherein R and $R_1$, which are the same or different, are polyamide residues bound on to the amido group and $R'_2$ is the residue of a compound which can be condensed with formaldehyde and also contains at least one further reactive group, this polyamide derivative then being reacted with a bi- or polyfunctional protein reagent and thereafter, in aqueous solution, brought together with a biologically active protein or a substrate thereof, with binding of the same.

The solvents used according to the present invention are those known for polyamides, for example lower aliphatic carboxylic acids and especially formic and acetic acid. The concentration of the solvent should be at least 10% and preferably at least 50%. Other solvents which can be used include 100% sulphuric acid, phosphoric acid, solutions of metal salts of the second Main Group of the Mendeleef Periodic Table, such as calcium chloride, in an alcohol, phenol, cresol, chloral hydrate or the like. The amount and concentration of the solvent depend, on the one hand, upon the polyamide used, and on the other hand, upon whether only a superficial dissolving is desired, i.e. the condensation in the presence of the formaldehyde proceeds in heterogeneous phase, or a complete dissolving of the polyamide is desired. Solvents which can be used for mixed polyamides include mixtures of aqueous alcohols with solubilizing agents, such as benzene or chlorinated hydrocarbons.

If only a superficial dissolving of a solid polyamide is carried out, then only a superficial condensing on takes place, without the shape of the polyamide being changed. The latter can, therefore, be, for example, in the form of a tube, granulate, foil or the like, and, according to the present invention, superficially bound with a biologically active protein. When carrying out the reaction in solution, the carbonamide groups are substituted on the polyamide by condensing on and subsequently the substituted polyamide formed is precipitated out with an appropriate precipitation agent, such as water or an aqueous solution of a bicarbonate. This method of working also provides the possibility of coating on any desired surfaces and especially on synthetic resin surfaces, which have been made sticky with an appropriate solvent (e.g. in the case of using polystyrene tubes, with benzene), with a solution of the substituted polyamide and subsequently activating the coated surface by reaction with the bi- or polyfunctional protein reagent and then using it for the protein binding.

According to a further embodiment of the present invention, in the case of only superficial dissolving of the polyamide, there can be used a solid carrier of any desired material, the surface of which is covered with finely-divided polyamide, for example in the form of a fabric, filaments, flocks, lints or the like. The polyamide particles can be stuck on to the carrier surface, applied by electrical flock deposition or attached thereto by other methods. In the case of this embodiment, large specific polyamide surfaces are present which, in the case of the protein fixing according to the present invention, give a high specific activity of the coated carrier. It is, of course, thereby necessary that only a superficial dissolving of the fine polyamide particles takes place, which keep their structure.

According to an especially preferred embodiment of the process of the present invention, in cases in which the compound which can be condensed with formaldehyde contains, as a further function, an amino group, coupling with the biologically active protein or protein substrate is carried out with the use of known amine coupling agents, such as phosgene, thiophosgene, cyanogen halides or nitrites. Such coupling agents are known for fixing biologically active proteins on to insoluble carrier materials which contain hydroxyl or amino groups. For example, when using a nitrite, the amino group is diazotised and the protein is then reacted with the diazo group. When using thiophosgene, the corresponding isothiocyanate is first formed which can then be reacted with an amino group of the protein, with immobilization thereof.

The process of the present invention can also be used for fixing not only biologically active proteins but also their substrates. For example, radioactively marked gelatine can be immobilized on a polyamide: a gelatine immobilized in this manner on polyamide can be used as a sensitive detection reagent for hydrolytic enzymes. Thus, for example, a synthetic resin reagent glass can be coated with marked gelatine bound on to polyamide, filled with a hydrolase solution and thereafter the marking going into the solution, for example radioactivity, can be determined.

The reaction of a compound of general formula (II) obtained according to the present invention with a protein reagent or with a coupling reagent and a biologically active protein or protein substrate can be carried out in one or more steps. In the case of a one-step reaction, a compound of general formula (II) is brought together with a biologically active protein or protein substrate and a coupling compound in aqueous solution and allowed to react. This procedure has the advantage of simplicity but frequently poorer yields are obtained than in the case of a multi-step method of working since, in this case, a part of the compound (II) can be coupled together and thus enters into undesired side reactions. In the case of a multi-step method of working, the coupling agent is first reacted with the compound (II) and the product obtained then reacted with the protein or protein substrate. Furthermore, the protein can be cross-linked with the protein coupling agent and separated off from non-cross-linked protein. The cross-linked protein is then reacted with the same or another protein coupling reagent and with the compound (II). The binding of such cross-linked protein derivatives gives especially high activities.

The first step of the process according to the present invention, i.e. the reaction in the presence of a compound which can be condensed with formaldehyde and in the presence of formaldehyde, can be carried out at temperatures of from about 0° to 100° C. When working in formic acid solution and in the presence of amines, then, as a competitive reaction, the Leuckart-Wallach reaction can take place. Therefore, under these conditions, it is preferable to work at lower temperatures within the scope of the above range.

By formaldehyde, there is to be understood, according to the present invention, the usual forms of formaldehyde, i.e. aqueous formaldehyde solutions, paraformaldehyde, trioxan and other formaldehyde polymers which, under the reaction conditions, behave as free formaldehyde. Trioxan is especially preferred since, as a solid and chemically clearly defined substance, it is the simplest to handle quantitatively.

The process according to the invention permits the immobilizing or fixing of biologically active proteins or of their substrates on carrier materials based on polyamides in an especially gentle manner and with the obtaining of advantageous properties. According to the present invention, the protein can be coupled directly on to a compound of general formula (II) formed as intermediate and also via intermediate compounds of any desired chosen size. The latter also permits the distance between the protein and the actual carrier molecule to be selected as desired. A comparatively large distance, i.e. the use of a comparatively long spacer, is, for example, of interest when already pre-cross-linked proteins are to be fixed, i.e. aggregates which consist of several molecules of biologically active proteins. For spatial reasons, a spacer which is as long as possible is then frequently necessary.

The immobilized biologically active proteins or protein substrates according to the present invention can be soluble or insoluble in aqueous solutions. For example, by coupling with water-soluble polyamides, the bleeding out of the protein through semipermeable membranes can be reduced or overcome, the stability can be increased or their usefulness as medicaments can become possible. In the case of coupling on to insoluble carrier materials, the simple recoverability of the biologically active protein is of outstanding importance. However, they can also be employed for obtaining antigens and antibodies as specific adsorption agents and in the field of enzymatic analysis.

The following Examples are given for the purpose of illustrating the present invention:

EXAMPLE 1

0.3 M Phenylenediamine and 0.1 M trioxan are mixed together in 50% formic acid and pumped for 3 hours through a 3 meter long tube of nylon-6. The tube is subsequently rinsed with water, filled with a 10% solution of glutardialdehyde in 0.2 M borate buffer (pH 8.5), left to stand for 15 minutes, again washed with water and then filled with a solution of 2 mg. glucose oxidase per ml. 0.1 M phosphate buffer (pH 7.8) and left to stand overnight at 4° C. After washing with 0.1 M phosphate buffer (pH=7.0), which is 1 M to sodium chloride, there is measured an enzymatic activity of 1.8 U/m. of tube.

EXAMPLE 2

20 g. Nylon flocks of 1 mm. length are suspended in 50% formic acid and reacted with 0.3 M phenylenediamine and 0.1 M trioxan for 3 hours at 50° C. The modified flocks are filtered off, washed and suspended in 1:10 dilute hydrochloric acid, cooled to 0° C. and, while stirring at 0° C., mixed with aqueous 2.5 M sodium nitrite solution. After 60 minutes, the flocks are washed with ice-cold water and a part thereof is immediately mixed with a solution of glucose oxidase containing 10 mg./ml. of phosphate buffer (pH 7.0). After fixing overnight at 4° C., the nylon flocks are subsequently washed with 1 M aqueous sodium chloride solution, whereafter they have an activity of 17 U/g.

A further part of the freshly diazotised derivative is mixed with a solution of α-foetoprotein antibodies in sodium carbonate buffer (pH 8) mixed with 0.1% of a tenside and left to stand overnight. The specific binding of the antibody is illustrated in the accompanying drawing.

EXAMPLES 3-5

Example 2 is repeated but using aniline, dianisidine or diaminodiphenylmethane instead of phenylenediamine. The specific binding of the antibodies is also illustrated in the accompanying drawing.

EXAMPLE 6

0.03 M Phenylenediamine and 0.01 M trioxan are dissolved in 50% acetic acid, heated to 60° C. and pumped for 3 hours through a 2 meter long nylon tube. The tube is subsequently washed with water and a 5% solution of a copolymer of methacrylamide and methacrylic acid hydroxysuccinimide ester is placed in the tube. After 4 hours, the tube is again emptied and washed with water. A solution of 2 mg. glucose oxidase per ml. of 0.1 M phosphate buffer (pH 7.8) is then placed in the tube and, after standing overnight at 4° C., the tube is emptied and washed. The final enzyme tube has an activity of 1.5 U/m.

EXAMPLE 7

20 g. amounts of nylon-6 particles are reacted for 2 hours with 0.3 M phenylenediamine and 0.1 M trioxan in 60% acetic acid solution at 50° C. or with 0.3 M diaminodiphenylmethane and 0.1 M trioxan in 60% acetic acid solution at 50° C. After washing with water, in each case half of the phenylenediamine product and of the diaminodiphenylmethane product is suspended 1:10 in dilute hydrochloric acid, cooled to 0° C. and diazotised with 2.5 M aqueous sodium nitrite solution at 0° C., while stirring. After 60 minutes, it is washed with ice-cold water. 1 g. amounts of the diazotised phenylenediamine derivative are mixed with a solution of 10 mg. glucose oxidase per ml. of 0.1 M phosphate buffer (pH 7.0) and left to stand overnight at 4° C. After washing with 0.1 M phosphate buffer (pH 7.0), which is 1 M to sodium chloride, there is found an activity, in the case of the phenylenediamine derivative, of 17 U/g. and, in the case of the diaminodiphenylmethane derivative, of 71 U/g. 1 g. amounts of the freshly diazotised phenylenediamine derivative and of the diaminodiphenylmethane derivative are mixed with a solution of 5 mg. cholesterol oxidase per ml. of 0.1 M phosphate buffer (pH 6.0), left to stand overnight at 4° C. and subsequently washed with 0.1 M phosphate buffer (pH 6.0), which is 1 M to sodium chloride. There is found an activity of 155 U/g. in the case of the diazotised phenylenediamine derivative and of 160 U/g. in the case of the diazotised diaminodiphenylmethane derivative. Subsequently, the two products are again washed with 0.1 M phosphate buffer (pH 6.0) which is 1 M to sodium chloride and 0.5% to thesite (hydroxypolyethoxydodecane). By means of this washing procedure, the activity of the phenylenediamine derivative decreases to 10 U/g. and that of the diaminodiphenylmethane derivative to 15 U/g.

EXAMPLE 8

5 g. amounts of nylon particles are reacted for 3 hours at 20° C. with, in each case, 0.3 M diaminodiphenylmethane and 0.1 M trioxan or 0.3 M urea and 0.1 M trioxan or 0.3 M aniline and 0.1 M trioxan or 0.3 M triaminotriazine and 0.1 M trioxan in 50% formic acid solution. After washing, the various derivatives are reacted for 15 minutes with 10% glutardialdehyde solution in 0.2 M borate buffer (pH 8.5) and again washed. 1 g. amounts of the various derivatives are thereafter mixed with 3 ml. of a kidney acylase solution containing 480 mg. in 40.5 ml. 0.1 M triethanolamine buffer (pH 8.3) for 1 hour and thereafter filtered off and washed. The mesured activity is, in the case of the phenylenediamine derivative, 7.5 U/g., in the case of the diaminodiphenylmethane, 6.7 U/g., in the case of urea, 6.8 U/g. and, in the case of triaminotriazine, 8.9 U/g.

EXAMPLE 9

10 g. Nylon-6 particles are reacted with a solution of 2 g. gelatin and 0.1 M trioxan in 50% formic acid solution for 3 hours at 50° C. The particles are subsequently washed and the nylon derivative is mixed with a 10% solution of glutardialdehyde in 0.2 M borate buffer (pH 8.5). After 15 minutes, the particles are filtered off and again washed and the nylon derivative obtained is mixed with a solution of 5 mg. glucose oxidase per ml. of 0.1 M phosphate buffer (pH 7.8). After standing overnight at 4° C., the material is filtered off and washed. The activity of the glucose oxidase bound on to the nylon derivative is 81 U/g.

EXAMPLE 10

0.1 M Polyamide-6 is dissolved in 100% formic acid and mixed with 0.1 M phenylenediamine and 0.033 M trioxan. After 3 hours at 50° C., the derivative formed is precipitated out with water and the precipitated nylon derivative, after washing with ethanol and water, is mixed with 10% glutardialdehyde solution in 0.2 M borate buffer (pH 8.5) for 15 minutes and again washed. Thereafter, the nylon derivative is added to a solution of 2 mg. glucose oxidase per ml. of 0.1 M phosphate buffer (pH 7.8), left to stand overnight at 4° C. and subsequently washed. The washed nylon derivative is subsequently found to have an activity of 16 U/g.

EXAMPLE 11

A nylon derivative is prepared as in Example 10 but, instead of being precipitated out with water, it is mixed with clay particles with a diameter of 0.315 to 0.400 mm., so that discrete particles are still present, and subsequently evacuated. After washing with water, the material is mixed with 10% glutardialdehyde solution in 0.2 M borate buffer (pH 8.5), after 15 minutes filtered off and washed and the coated clay mixed with a solution of 2 mg. glucose oxidase per ml. 0.1 M phosphate buffer (pH 7.8). After standing overnight at 4° C., filtering off and washing, the nylon-clay derivative has a glucose oxidase activity of 8 U/g.

EXAMPLE 12

A nylon derivative is prepared as in Example 10 and placed in polystyrene test tubes of 3 cm. height and 1 cm. diameter which have previously been made sticky with benzene. After leaving to stand for one hour, the tubes are emptied and rinsed, then filled with a 10% solution of glutardialdehyde in 0.2 M borate buffer (pH 8.5). After 15 minutes, the tubes are again emptied, rinsed and filled with a solution of 2 mg. glucose oxidase per ml. of 0.1 M phosphate buffer (pH 7.8). After standing overnight at 4° C., the test tubes are washed and subsequently exhibit an activity of 0.5 U/test tube.

EXAMPLE 13

Polyamide-6 is dissolved at a temperature of 30° to 80° C. in a mixture of 18.6 g. calcium chloride and 18.6 g. water, together with 63 g. methanol and 1 to 1000 parts formic acid and filled, while still hot, into 2 meter long nylon-6 tubes and thereafter immediately rinsed with cold water. A layer of amorphous, reactive nylon remains behind on the inner surface of the tube. A solution of 0.03 M phenylenediamine and 0.01 M trioxan in 60% acetic acid is then pumped through the tube at 60° C. Subsequently, the tube is washed with water and then a solution of 50 mg. suberic acid dihydroxysuccinimide ester in 1 ml. dioxan placed into the tube. After 15 hours, the tube is emptied and
 (a) a solution of 5 mg. glucose oxidase per ml. of 0.1 M phoshate buffer (pH 7.8) introduced,
 (b) a solution of 372 mg. glucose oxidase in 4.5 ml. 0.1 M phosphate buffer (pH 7.8) is mixed with 6.4 mg. ethyleneglycol bis-propionic acid bis-hydroxysuccinimide ester in 0.5 ml. dioxan and left to stand overnight at 4° C. Thereafter, the cross-linked glucose oxidase is chromatographed over a column of "Sephadex" G200 (cross-linked dextran) ("Sephadex" is a Registered Trade Mark) and the cross-linked part (about 90% in the determined volume), in 0.1 M phosphate buffer (pH 7.8), is placed into the above prepared tube.

In the case of (a), there is found an activity of 4 U/m. and in the case of (b) an activity of 9 U/m.

EXAMPLE 14

10 g. Nylon-6 particles of 0.100 to 0.125 mm. diameter are suspended in 100 ml. 40% formic acid and 2.25 g. trioxan (0.075 mol formaldehyde units) and 9.4 g. phenol (0.1 mol) are added thereto. After 3 hours at 50° C., the particles are filtered off with suction, washed with methanol and then subsequently washed with dry diethyl ether. The particles are suspended in 250 ml. toluene in which are dissolved 10 ml. hexamethylene diisocyanate. After 2 hours, the particles are filtered off with suction, subsequently rinsed with dry diethyl ether and immediately a solution of 5 mg. glucose oxidase per ml. of 0.1 M phosphate buffer (pH 7.0) added to the particles. After standing overnight, the particles are washed. The subsequently measured activity is found to be 11.2 U/g.

It will be understood that the specification and examples are illustrative, but not limitative of the present invention and that other embodiments within the spirit and scope of the invention will suggest themselves to those skilled in the art.

What is claimed is:

1. Biologically active protein composition comprising protein or a protein substrate bound onto a polyamide, of the formula

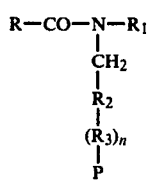

in which
R and $R_1$, which may be the same or different, are polyamide residues bound onto the amido group,
$R_2$ is the residue of a compound which can be condensed with formaldehyde and which contains at least one further reactive group,
$R_3$ is the residue of a bi- or poly-functional protein reagent,
n is 0 or 1, and
P is a biologically active protein
wherein said composition is obtained by the reaction of polyamide with equal moles of formaldehyde and a compound which can be condensed with formaldehyde in a solvent for polyamides, and reacting the resulting product with a bi- or poly-functional protein reagent selected from dialdehydes, dihydroxysuccinimide esters, diacetals, bis-maleinimides, bifunctional imino esters, diepoxides and dicarboxylic acid chlorides, and then coupling the resulting product with a biologically active protein or protein substrate.

2. Biologically active protein composition as claimed in claim 1 wherein R is a polycaprolactam residue.

3. Biologically active protein composition as claimed in claim 1 wherein R is a residue of a polyamide selected from 6,6-polyamide, 6,10-polyamide, 11-polyamide, or 12-polyamide.

4. Biologically active protein composition as claimed in claim 1 wherein $R_1$ is a polycaprolactam residue.

5. Biologically active protein composition as claimed in claim 1 wherein $R_1$ is a residue of a polyamide selected from 6,6-polyamide, 6,10-polyamide, 11-polyamide, or 12-polyamide.

6. Biologically active protein composition as claimed in claim 1 wherein $R_2$ is derived from phenol or aniline.

7. Biologically active protein composition as claimed in claim 1 wherein $R_2$ is derived from urea or thiourea.

8. Biologically active protein composition as claimed in claim 1 wherein $R_2$ is derived from melamine.

9. Biologically active protein composition as claimed in claim 1 wherein $R_2$ is derived from diaminotriazine.

10. Biologically active protein composition as claimed in claim 1 wherein $R_2$ is derived from aliphatic, aromatic or araliphatic diamine containing from 2 to 14 carbon atoms.

11. Biologically active protein composition as claimed in claim 1 wherein $R_3$ is derived from glutardialdehyde.

12. Biologically active protein composition as claimed in claim 1 wherein $R_3$ is derived from a dihydroxysuccinimide ester.

13. Biologically active protein composition as claimed in claim 1 wherein $R_3$ is derived from a diacetal.

14. Biologically active protein composition as claimed in claim 1 wherein $R_3$ is derived from bis-maleinimide.

15. Biologically active protein composition as claimed in claim 1 wherein $R_3$ is derived from a bi-functional imino ester.

16. Biologically active protein composition as claimed in claim 1 wherein $R_3$ is derived from a diepoxide.

17. Biologically active protein composition as claimed in claim 1 wherein $R_3$ is derived from a dicarboxylic acid chloride.

18. Biologically active protein composition as claimed in claim 1 wherein $R_3$ is derived from a copolymer of acrylamide/methacrylamide and acrylic acid succinimide ester/methacrylic acid succinimide ester.

19. Process for fixing a biologically active protein composition comprising a protein or a protein substrate onto a polyamide which process comprises reacting the polyamide, in the presence of a solvent for polyamides, with amounts, equimolar to one another, of formaldehyde and of a compound which can be condensed with formaldehyde and contains at least one further reactive group, to result in the formation of a polyamide derivative of the formula

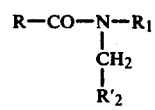

wherein
R and $R_1$, which are the same or different, are polyamide residues bound onto the amido group, and
$R_2$ is the residue of a compound which can be condensed with formaldehyde which contains at least one further reactive group,
then reacting said polyamide derivative with a bi- or poly-functional protein reagent, and thereafter bringing the resulting reaction product together with a biologically active protein or protein substrate, in aqueous solution, to result in binding thereof to said reaction product.

20. Process as claimed in claim 19 wherein the reaction with the formaldehyde is carried out in at least 50% formic acid or acetic acid.

21. Process as claimed in claim 19 wherein the polyamide is used in the form of a shaped body of which only the surface is dissolved.

22. Process as claimed in claim 19 wherein the reaction is carried by depositing the said polyamide derivative on a solid carrier surface.

23. Process as claimed in claim 21 wherein said shaped body is a solid carrier material the surface of which is coated with finely divided polyamide.

24. Process as claimed in claim 19 wherein said active protein or protein substrate is bound by reaction with nitrite and diazotization.

25. Process as claimed in claim 19 wherein said active protein or protein substrate is bound by means of phosgene, thiophosgene or cyanogen halide.

26. Process as claimed in claim 19 wherein said protein is a cross-linked protein.

* * * * *